(12) United States Patent
Watson et al.

(10) Patent No.: US 8,928,230 B2
(45) Date of Patent: Jan. 6, 2015

(54) COLD PLASMA TREATMENT DEVICES AND ASSOCIATED METHODS

(75) Inventors: Gregory A. Watson, Sanford, FL (US); Marc C. Jacofsky, Phoenix, AZ (US)

(73) Assignee: Cold Plasma Medical Technologies, Inc., Scottsdale, AZ (US)

(*) Notice: Subject to any disclaimer, the term of this patent is extended or adjusted under 35 U.S.C. 154(b) by 0 days.

(21) Appl. No.: 13/620,224

(22) Filed: Sep. 14, 2012

(65) Prior Publication Data

US 2013/0072861 A1 Mar. 21, 2013

Related U.S. Application Data

(60) Provisional application No. 61/535,250, filed on Sep. 15, 2011.

(51) Int. Cl.
| | |
|---|---|
| H01J 7/24 | (2006.01) |
| A61M 16/12 | (2006.01) |
| H01J 37/32 | (2006.01) |
| A61M 15/02 | (2006.01) |
| A61N 1/44 | (2006.01) |
| H05H 1/24 | (2006.01) |

(52) U.S. Cl.
CPC ............ *A61M 16/12* (2013.01); *H05H 2240/20* (2013.01); *A61M 2202/025* (2013.01); *H01J 37/32348* (2013.01); *A61N 1/44* (2013.01); *A61M 2202/0208* (2013.01); *H05H 2001/2412* (2013.01); *A61M 15/02* (2013.01); *H05H 1/2406* (2013.01)
USPC ............. 315/111.91; 315/111.21; 315/111.81

(58) Field of Classification Search
USPC ........................... 315/111.51, 111.21, 111.91
See application file for complete search history.

(56) References Cited

U.S. PATENT DOCUMENTS

| | | | |
|---|---|---|---|
| 2,927,322 | A | 3/1960 | Simon et al. |
| 3,432,722 | A | 3/1969 | Naydan et al. |
| 3,487,414 | A | 12/1969 | Booker |
| 3,735,591 | A | 5/1973 | Burkhart |
| 4,088,926 | A | 5/1978 | Fletcher et al. |

(Continued)

FOREIGN PATENT DOCUMENTS

| | | |
|---|---|---|
| JP | 2006-244938 | 9/2006 |
| WO | WO 2005/084569 A1 | 9/2005 |

(Continued)

OTHER PUBLICATIONS

International Search Report mailed Nov. 30, 2012 for Appl. No. PCT/US2012/55602, 3 pages.

(Continued)

*Primary Examiner* — Douglas W Owens
*Assistant Examiner* — Srinivas Sathiraju
(74) *Attorney, Agent, or Firm* — Sterne, Kessler, Goldstein & Fox P.L.L.C.

(57) ABSTRACT

A cold plasma treatment device for delivery of a cold plasma to patient treatment area. Gas is fed to a gas compartment where it is energized by an electrode coupled to a pulse source to thereby generate a cold plasma. A dielectric barrier is sandwiched between the gas compartment and the electrode to form a dielectric barrier discharge device. The cold plasma exits the gas compartment via a bottom member having a plurality of holes. Gases that can be used include noble gases such as helium or combinations of noble gases.

22 Claims, 9 Drawing Sheets

(56) References Cited

U.S. PATENT DOCUMENTS

| | | | |
|---|---|---|---|
| 4,365,622 A | | 12/1982 | Harrison |
| 4,380,320 A | | 4/1983 | Hollstein et al. |
| 4,422,013 A | | 12/1983 | Turchi et al. |
| 5,079,482 A | | 1/1992 | Villecco et al. |
| 5,216,330 A | | 6/1993 | Ahonen |
| 5,225,740 A | | 7/1993 | Ohkawa |
| 5,304,888 A | | 4/1994 | Gesley et al. |
| 5,698,164 A | | 12/1997 | Kishioka et al. |
| 5,876,663 A | | 3/1999 | Laroussi |
| 5,883,470 A | | 3/1999 | Hatakeyama et al. |
| 5,909,086 A | | 6/1999 | Kim et al. |
| 5,961,772 A | * | 10/1999 | Selwyn ................ 156/345.39 |
| 5,977,715 A | | 11/1999 | Li et al. |
| 6,096,564 A | * | 8/2000 | Denes et al. .................. 438/1 |
| 6,113,851 A | | 9/2000 | Soloshenko et al. |
| 6,204,605 B1 | | 3/2001 | Laroussi et al. |
| 6,225,593 B1 | | 5/2001 | Howieson et al. |
| 6,228,330 B1 | | 5/2001 | Herrmann et al. |
| 6,262,523 B1 | | 7/2001 | Selwyn et al. |
| 6,441,554 B1 | | 8/2002 | Nam et al. |
| 6,611,106 B2 | | 8/2003 | Monkhorst et al. |
| 6,667,007 B1 | | 12/2003 | Schmidt |
| 6,956,329 B2 | | 10/2005 | Brooks et al. |
| 6,958,063 B1 | * | 10/2005 | Soll et al. .................... 606/41 |
| 7,006,874 B2 | | 2/2006 | Knowlton et al. |
| 7,011,790 B2 | | 3/2006 | Ruan et al. |
| 7,081,711 B2 | | 7/2006 | Glidden et al. |
| 7,094,314 B2 | | 8/2006 | Kurunczi |
| 7,192,553 B2 | | 3/2007 | Crowe et al. |
| 7,215,697 B2 | | 5/2007 | Hill |
| 7,271,363 B2 | | 9/2007 | Lee et al. |
| 7,300,436 B2 | | 11/2007 | Penny et al. |
| 7,608,839 B2 | | 10/2009 | Coulombe et al. |
| 7,633,231 B2 | | 12/2009 | Watson |
| 7,683,342 B2 | | 3/2010 | Morfill et al. |
| 7,691,101 B2 | | 4/2010 | Davison et al. |
| 7,719,200 B2 | | 5/2010 | Laroussi |
| 7,777,151 B2 | | 8/2010 | Kuo |
| 7,785,322 B2 | | 8/2010 | Penny et al. |
| 8,267,884 B1 | * | 9/2012 | Hicks .......................... 604/23 |
| 8,294,369 B1 | | 10/2012 | Laroussi |
| 8,460,283 B1 | * | 6/2013 | Laroussi et al. ............ 606/34 |
| 2002/0129902 A1 | * | 9/2002 | Babayan et al. ......... 156/345.45 |
| 2003/0222586 A1 | | 12/2003 | Brooks et al. |
| 2005/0088101 A1 | | 4/2005 | Glidden et al. |
| 2005/0179395 A1 | | 8/2005 | Pai |
| 2006/0189976 A1 | | 8/2006 | Karni et al. |
| 2008/0145553 A1 | | 6/2008 | Boulos et al. |
| 2008/0159925 A1 | | 7/2008 | Shimizu et al. |
| 2009/0188626 A1 | | 7/2009 | Lu et al. |
| 2010/0133979 A1 | | 6/2010 | Lu |
| 2011/0022043 A1 | | 1/2011 | Wandke et al. |
| 2011/0042560 A1 | | 2/2011 | Ouyang et al. |
| 2012/0187841 A1 | | 7/2012 | Kindel et al. |
| 2012/0259270 A1 | | 10/2012 | Wandke et al. |
| 2013/0053762 A1 | * | 2/2013 | Rontal et al. ................ 604/24 |
| 2013/0134878 A1 | * | 5/2013 | Selwyn ................... 315/111.21 |
| 2013/0199540 A1 | * | 8/2013 | Buske .......................... 128/845 |

FOREIGN PATENT DOCUMENTS

| | | |
|---|---|---|
| WO | WO 2006/116252 | 11/2006 |
| WO | WO 2011/055368 A2 | 5/2011 |
| WO | WO 2011/055369 A2 | 5/2011 |
| WO | WO 2011/076193 A1 | 6/2011 |
| WO | WO 2012/153332 A2 | 11/2012 |

OTHER PUBLICATIONS

Written Opinion of International Searching Authority mailed Nov. 30, 2012 for Appl. No. PCT/US2012/55602, 3 pages.

English-language abstract for: Ryuichiro et al. JP 2006-244938, Sep. 14, 2006, 2 pages.

Dumé, Belle, "Cold Plasmas Destroy Bacteria," article, [online], [retrieved on Jan. 5, 2007], Retrieved from the PhysicsWeb website using Internet <URL:http://physicsweb.org/articles/news7/4/19>.

Gould, Ohilip and Eyler, Edward, "Ultracold Plasmas Come of Age," article [online], [retrieved on Jan. 5, 2007], Retrieved from the PhysicsWeb website using Internet <URL:http://physicsweb.org/articles/world/14/3/3>.

Schultz, James, "Cold Plasma Ignites Hot Applications," article, [online], [retrieved on Jan. 5, 2007], Retrieved from the Old Dominion University website using Internet <URL:http://www.odu.edu/ao/instadv/quest/coldplasma.html>.

Lamba, Bikram, "Advent of Cold Plasma," article, [online], [retrieved on Jan. 5, 2007], Retrieved from the PhysOrg.com website using Internet <URL:http//www.physorg.com/printnews.php?newsid=6688>.

Book of Abstracts, 3rd International Conference on Plasma Medicine (ICPM-3), Sep. 19-24, 2010, Internatioanl Society for Plasma Medicine.

International Search Report issued Aug. 6, 2008 for Appl. No. PCT/US2008/061240, 1 page.

Written Opinion of International Searching Authority issued Aug. 6, 2008 for Appl. No. PCT/US2008/061240, 6 pages.

Extended European Search Report issued Feb. 8, 2012 for European Patent Appl. No. EP08746627.2, 7 pages.

Pointu et al., "Nitrogen Atmospheric Pressure Post Discharges for Surface Biological Decontamination inside Small Diameter Tubes," *Plasma Process. Polym.* 5:559-568, Wiley-VCH Verlag GmbH & Co. KGaA, Weinheim (2008).

Chakravarthy et al., "Cold Spark Discharge Plasma Treatment of Inflammatory Bowel Disease in an Animal Model of Ulcerative Colitis," *Plasma Medicine* (1)1:36-19, Begell House, Inc. (2011).

Fridman et al., "Comparison of Direct and Indirect Effects of Non-Thermal Atmospheric-Pressure Plasma on Bacteria," *Plasma Processl Polym.*, 4, 370-375, 6 pages, Wiley-VCH Verlag GmbH & Co. KGaA, Weinheim (2007).

Alexander Fridman, "Plasma Chemistry," pp. 263-271, Cambridge University Press, 2008, 9 pages.

O'Connell et al., "The role of the relative voltage and phase for frequency coupling in a dual-frequency capacitively coupled plasma," *Applied Physics Letters*, 93 081502, 3 pages, American Institute of Physics (Aug. 25, 2008).

Nie et al., "A two-dimensional cold atmospheric plasma jet array for uniform treatment of large-area surfaces for plasma medicine," *New Journal of Physics*, 11 115015, 14 pages, IOP Publishing Ltd and Deutsche Physikalische Gesellschaft (2009).

Pompl et al., "The effect of low-temperature plasma on bacteria as observed by repeated AFM imaging," *New Journal of Physics*, 11 115023, 11 pages, IOP Publishing Ltd and Deutsche Physikalische Gesellschaft (Nov. 26, 2009).

Walsh et al., "Three district modes in a cold atmospheric pressure plasma jet," *J. Phys. D.: Appl. Phys.* 43 075201, 14 pages, IOP Publishing Ltd (Feb. 3, 2010).

Ricci et al., "The effect of stochastic electrical noise on hard-to-heal wounds," *Journal of Wound Care*, 8 pages, 19:3 Mark Allen Publishing Ltd (Mar. 2010).

U.S. Appl. No. 61/485,747, filed May 13, 2011, inventor Thomas J. Sheperak, 14 pages.

Liu et al., "Sub-60° C. atmospheric helium-water plasma jets: modes, electron heating and downstream reaction chemistry," *J. Phys. D.: Appl. Phys.* 44 345203, 13 pages, IOP Publishing Ltd. (Aug. 11, 2011).

Pei et al., "Inactivation of a 25.5 μm *Enterococcus faecalis* biofilm by a room-temperature, battery-operated, handheld air plasma jet," *J. Phys. D. Appl. Phys.*, 45 165205, 5 pages, IOP Publishing Ltd (Apr. 4, 2012).

Walsh et al., "Chaos in atmospheric-pressure plasma jets," *Plasma Sources Sci. Technol.*, 21 034008, 8 pages, IOP Publishing Ltd (May 2, 2012).

\* cited by examiner

COLD PLASMA TREATMENT DEVICES AND ASSOCIATED METHODS

CROSS REFERENCE TO RELATED APPLICATIONS

The present application claims the benefit under 35 U.S.C. §119(e) of U.S. Provisional Patent Application No. 61/535,250, entitled "Harmonic Cold Plasma Devices and Associated Methods", filed on Sep. 15, 2011, which is hereby expressly incorporated by reference in its entirety.

This application is related to U.S. patent application Ser. No. 13/149,744, filed May 31, 2011, U.S. patent application Ser. No. 12/638,161, filed Dec. 15, 2009, U.S. patent application Ser. No. 12/038,159, filed Feb. 27, 2008, and U.S. Provisional Application No. 60/913,369, filed Apr. 23, 2007, each of which are herein incorporated by reference in their entireties.

BACKGROUND

1. Field of the Art

The present invention relates to devices and methods for creating cold plasmas, and, more particularly, to cold plasma treatment methods and application devices.

2. Background Art

Atmospheric pressure hot plasmas are known to exist in nature. For example, lightning is an example of a DC arc (hot) plasma. Many DC arc plasma applications have been achieved in various manufacturing processes, for example, for use in forming surface coatings. Atmospheric pressure cold plasma processes are also known in the art. Most of the at or near atmospheric pressure cold plasma processes are known to utilize positive to negative electrodes in different configurations, which release free electrons in a noble gas medium.

Devices that use a positive to negative electrode configuration to form a cold plasma from noble gases (helium, argon, etc.) have frequently exhibited electrode degradation and overheating difficulties through continuous device operation. The process conditions for enabling a dense cold plasma electron population without electrode degradation and/or overheating are difficult to achieve.

Different applications of cold plasma devices require different size cold plasma plumes and different dimensional devices to produce those cold plasma plumes. For example, some medical treatments require a large cold plasma plume to treat a large external wound, while other treatments require a small cold plasma device that can be coupled to an elongated medical device that can traverse a small body passageway to reach a small internal treatment site.

BRIEF SUMMARY OF THE INVENTION

There is a need to address large treatment areas, such as burns, skin graft donor and recipient sites, tissue flaps, and the like. For a cold plasma treatment device to be able to address such large treatment areas, the cold plasma treatment device needs to be able to provide a stable cold plasma plume with a size that is commensurate with the treatment area.

An embodiment of a cold plasma treatment device is described that includes a body having a gas compartment therein. The gas compartment is communicatively coupled to a gas inlet port. A bottom member of the cold plasma treatment device has a plurality of openings that are communicatively coupled to the gas compartment. A dielectric barrier discharge device is formed by an electrode disposed adjacent to an insulating barrier, the insulating barrier in turn disposed adjacent to the gas compartment and the electrode coupled to a high voltage electrical inlet port.

Another embodiment is described regarding a method of generating a cold plasma. A gas is received into a gas compartment within a body, the gas being received via a gas inlet port. The received gas is energized within the gas compartment to generate a cold plasma by applying electrical energy via an electrical input port to an electrode adjacent to a dielectric barrier, the dielectric barrier being sandwiched between the electrode and the gas compartment. The cold plasma is output via a plurality of holes in a bottom member, the plurality of holes being communicatively coupled to the gas compartment.

DETAILED DESCRIPTION OF THE INVENTION

Cold temperature atmospheric pressure plasmas have attracted a great deal of enthusiasm and interest by virtue of their provision of plasmas at relatively low gas temperatures. The provision of a plasma at such a temperature is of interest to a variety of applications, including wound healing, antibacterial processes, various other medical therapies and sterilization.

Cold Plasma Application Device

Figure 1A:
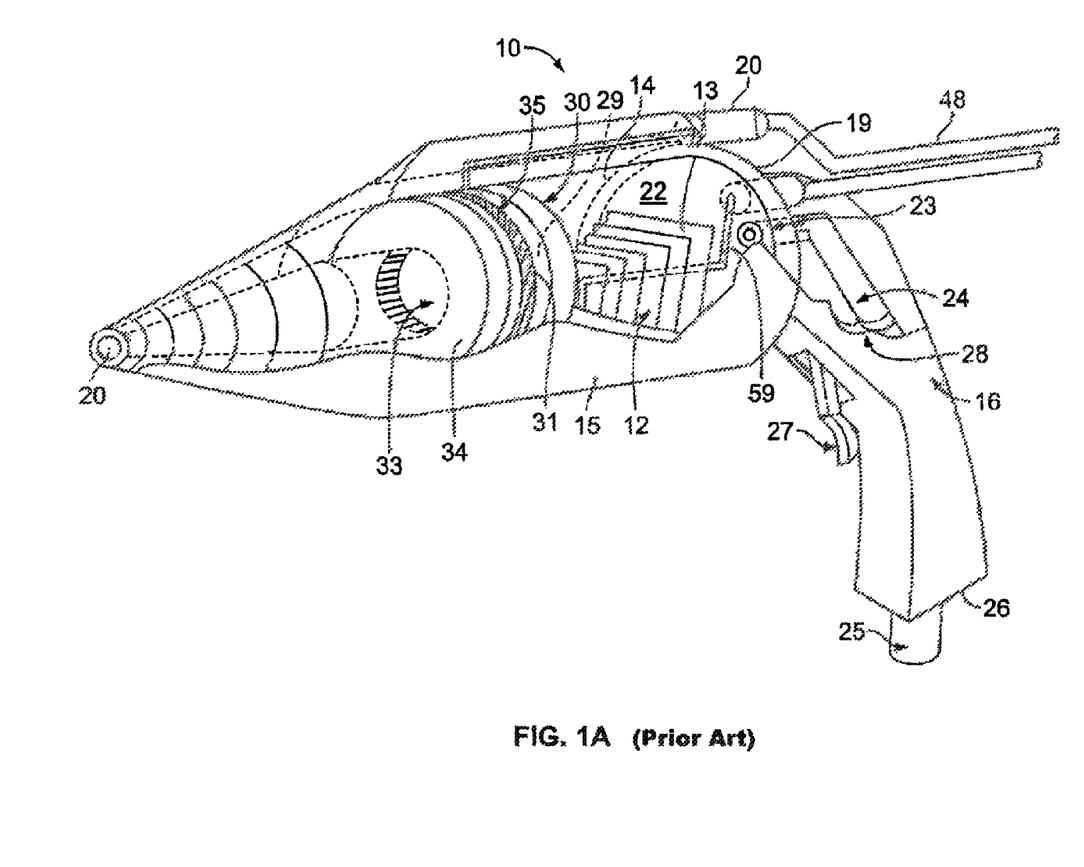
FIGS. 1A and 1B is a cutaway view of the hand-held atmospheric harmonic cold plasma device, in accordance with embodiments of the present invention.

To achieve a cold plasma, a cold plasma device typically takes as input a source of appropriate gas and a source of high voltage electrical energy, and outputs a plasma plume. FIG. 1A illustrates such a cold plasma device. Previous work by the inventors in this research area has been described in U.S. Provisional Patent Application No. 60/913,369, U.S. Nonprovisional application Ser. No. 12/038,159 (that has issued as U.S. Pat. No. 7,633,231) and the subsequent continuation applications (collectively "the '369 application family"). The following paragraphs discuss further the subject matter from this application family further, as well as additional developments in this field.

The '369 application family describes a cold plasma device that is supplied with helium gas, connected to a high voltage energy source, and which results in the output of a cold plasma. The temperature of the cold plasma is approximately 65-120 degrees F. (preferably 65-99 degrees F.), and details of the electrode, induction grid and magnet structures are described. The voltage waveforms in the device are illustrated at a typical operating point in '369 application family.

Figure 1B:
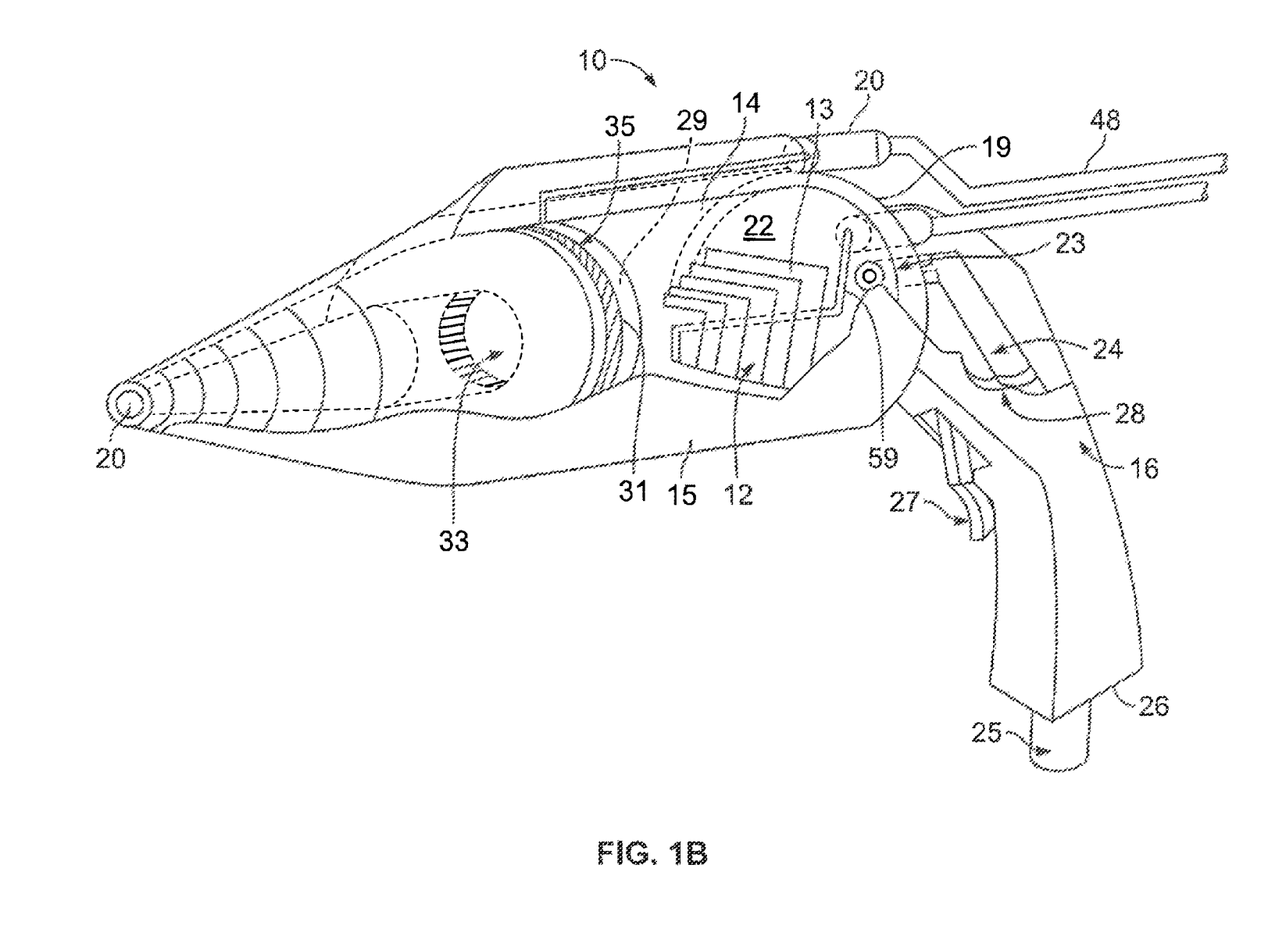
Figure 2A:
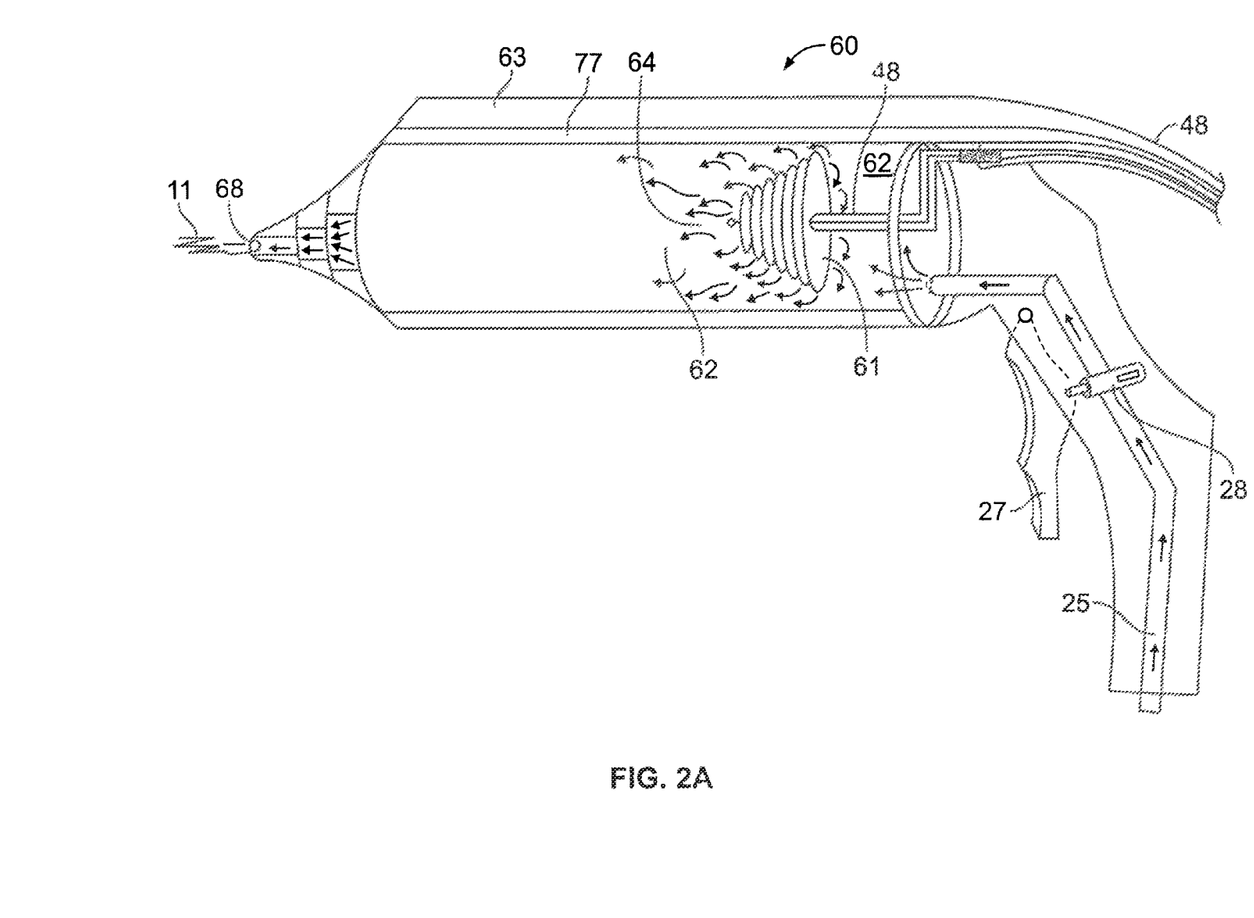
FIGS. 2A and 2B illustrate an embodiment of the cold plasma device without magnets, in accordance with embodiments of the present invention.
Figure 2B:
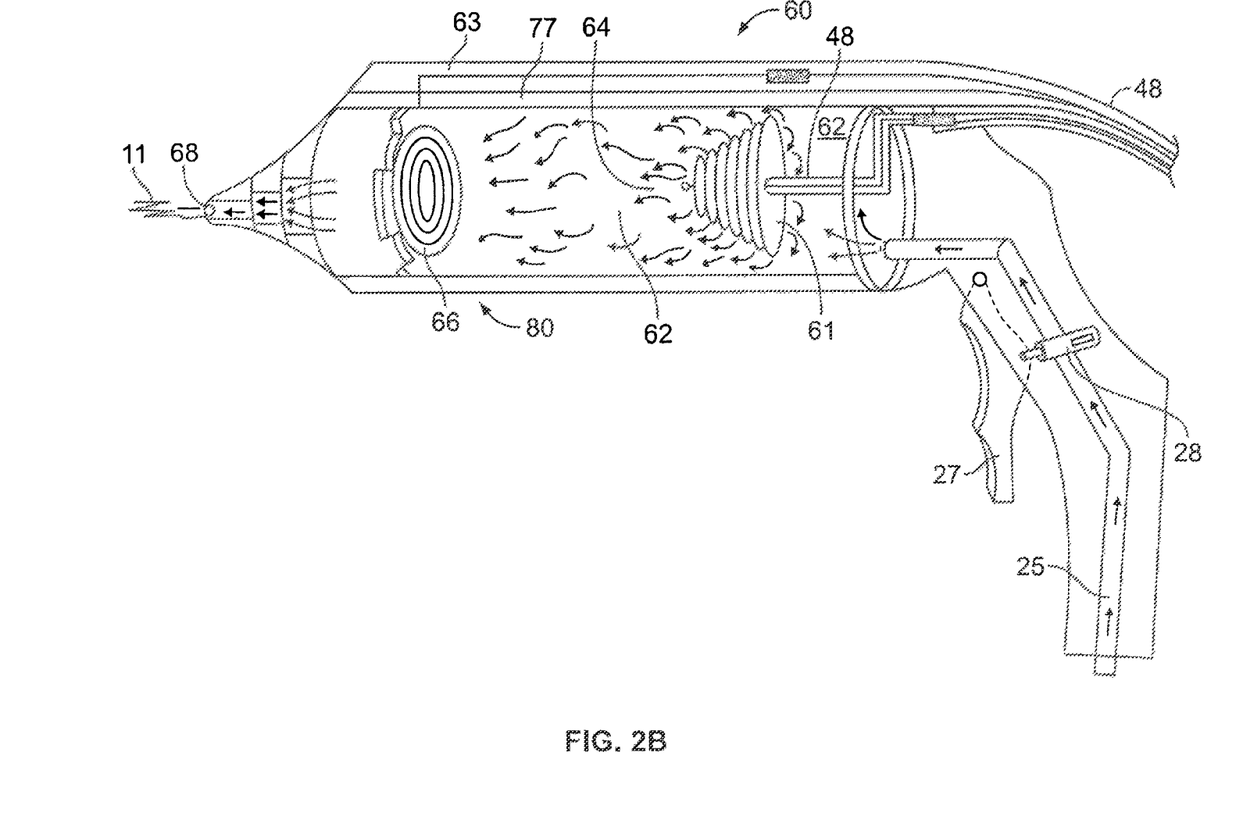

In a further embodiment to that described in the '369 application, plasma is generated using an apparatus without magnets, as illustrated in FIGS. 2A and 2B. In this magnet-free environment, the plasma generated by the action of the electrodes 61 is carried with the fluid flow downstream towards the nozzle 68. FIG. 2A illustrates a magnet-free embodiment in which no induction grid is used. FIG. 2B illustrates a magnet-free embodiment in which induction grid 66 is used. FIG. 1B illustrates the same embodiment as illustrated FIG. 2B, but from a different view. Although these embodiments illustrate the cold plasma is generated from electrode 12, other embodiments do not power the cold plasma device using electrode 12, but instead power the cold plasma device using induction grid 66.

In both a magnet and a magnet-free embodiment, the inductance grid 66 is optional. When inductance grid 66 is present, it provides ionization energy to the gas as the gas passes by. Thus, although the inductance grid 66 is optional, its presence enriches the resulting plasma.

As noted above, the inductance grid 66 is optional. When absent, the plasma will nevertheless transit the cold plasma device and exit at the nozzle 68, although in this case, there will be no additional ionization energy supplied to the gas as it transits the latter stage of the cold plasma device.

As noted with respect to other embodiments, magnetic fields can be used in conjunction with the production of cold plasmas. Where present, magnetic fields act, at least at some level, to constrain the plasma and to guide it through the device. In general, electrically charged particles tend to move along magnetic field lines in spiral trajectories. As noted elsewhere, other embodiments can comprise magnets configured and arranged to produce various magnetic field configurations to suit various design considerations. For example, in one embodiment as described in the previously filed '369 application family, a pair of magnets may be configured to give rise to magnetic fields with opposing directions that act to confine the plasma near the inductance grid.

Cold Plasma Unipolar High Voltage Power Supply

The '369 application family also illustrates an embodiment of the unipolar high voltage power supply architecture and components used therein. The circuit architecture is reproduced here as FIG. 3, and this universal power unit provides electrical power for a variety of embodiments described further below. The architecture of this universal power unit includes a low voltage timer, followed by a preamplifier that feeds a lower step-up voltage transformer. The lower step-up voltage transformer in turn feeds a high frequency resonant inductor-capacitor (LC) circuit that is input to an upper step-up voltage transformer. The output of the upper step-up voltage transformer provides the output from the unipolar high voltage power supply.

Figure 3:
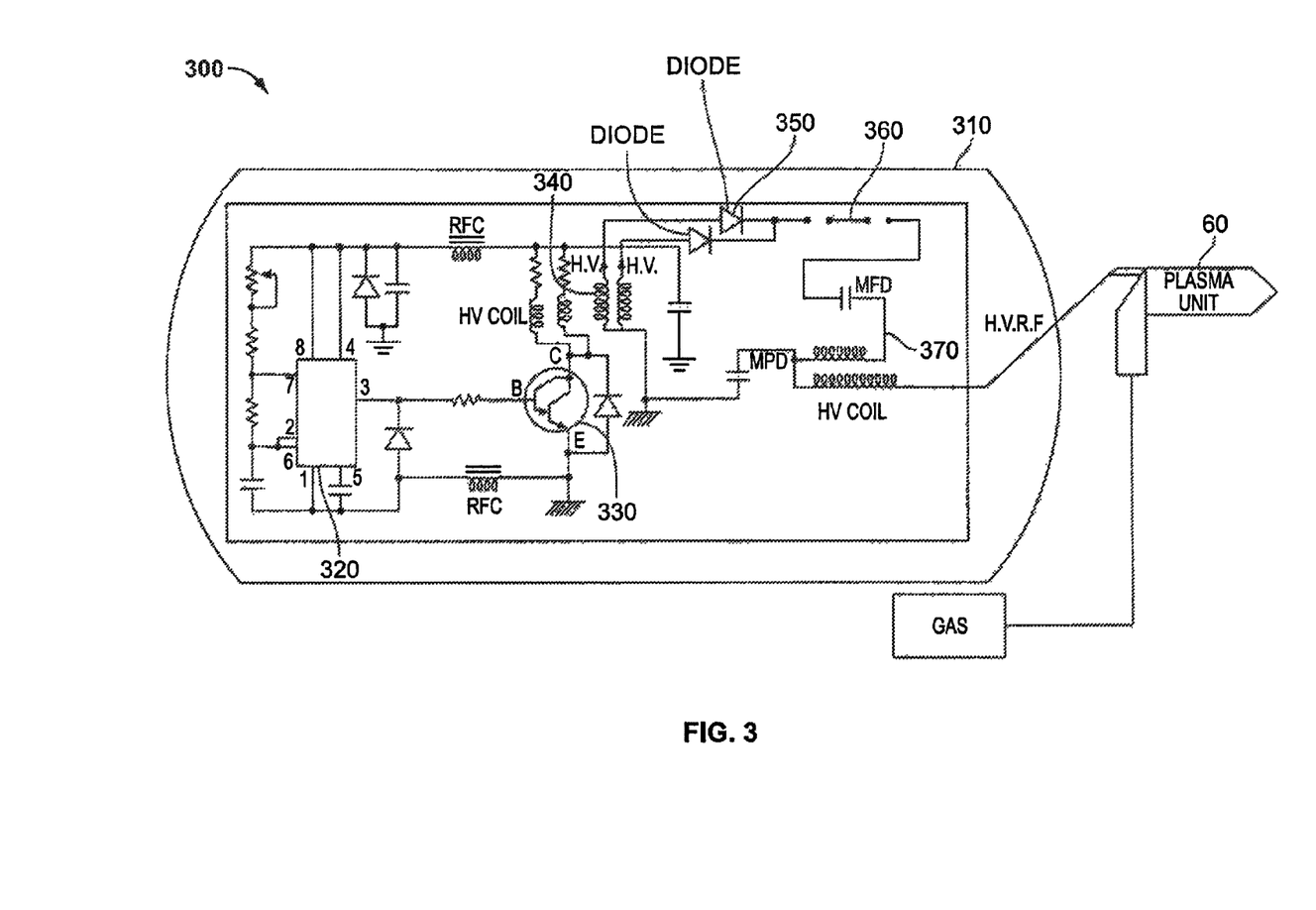
FIG. 3 is an exemplary circuit diagram of the power supply of a cold plasma device, in accordance with embodiments of the present invention.

FIG. 3 also illustrates an exemplary implementation of the unipolar high voltage power supply 310 architecture. In this implementation, a timer integrated circuit such as a 555 timer 320 provides a low voltage pulsed source with a frequency that is tunable over a frequency range centered at approximately 1 kHz. The output of the 555 timer 320 is fed into a preamplifier that is formed from a common emitter bipolar transistor 330 whose load is the primary winding of the lower step-up voltage transformer 340. The collector voltage of the transistor forms the output voltage that is input into the lower step-up voltage transformer. The lower step-up transformer provides a magnification of the voltage to the secondary windings. In turn, the output voltage of the lower step-up voltage transformer is forwarded to a series combination of a high voltage rectifier diode 350, a quenching gap 360 and finally to a series LC resonant circuit 370. As the voltage waveform rises, the rectifier diode conducts, but the quench gap voltage will not have exceeded its breakdown voltage. Accordingly, the quench gap is an open circuit, and therefore the capacitor in the series LC resonant circuit will charge up. Eventually, as the input voltage waveform increases, the voltage across the quench gap exceeds its breakdown voltage, and it arcs over and becomes a short circuit. At this time, the capacitor stops charging and begins to discharge. The energy stored in the capacitor is discharged via the tank circuit formed by the series LC connection.

Continuing to refer to FIG. 3, the inductor also forms the primary winding of the upper step-up voltage transformer 340. Thus, the voltage across the inductor of the LC circuit will resonate at the resonant frequency of the LC circuit 370, and in turn will be further stepped-up at the secondary winding of the upper step-up voltage transformer. The resonant frequency of the LC circuit 370 can be set to in the high kHz-low MHz range. The voltage at the secondary winding of the upper step-up voltage transformer is connected to the output of the power supply unit for delivery to the cold plasma device. The typical output voltage is in the 10-150 kV voltage range. Thus, voltage pulses having a frequency in the high kHz-low MHz range can be generated with an adjustable repetition frequency in the 1 kHz range. The output waveform is shaped similar to the acoustic waveform generated by an impulse such as a bell is struck with a hammer. Here, the impulse is provided when the spark gap (or SCR) fires and produces the voltage pulse which causes the resonant circuits in the primary and secondary sides of the transformer to resonate at their specific resonant frequencies. The resonant frequencies of the primary and the secondary windings are different. As a result, the two signals mix and produce the unique 'harmonic' waveform seen in the transformer output. The net result of the unipolar high voltage power supply is the production of a high voltage waveform with a novel "electrical signature," which when combined with a noble gas or other suitable gas, produces a unique harmonic cold plasma that provides advantageous results in wound healing, bacterial removal and other applications.

The quenching gap 360 is a component of the unipolar high voltage power supply 310. It modulates the push/pull of electrical energy between the capacitance banks, with the resulting generation of electrical energy that is rich in harmonic content. The quenching gap can be accomplished in a number of different ways, including a sealed spark gap and an unsealed spark gap. The sealed spark gap is not adjustable, while unsealed spark gaps can be adjustable. A sealed spark gap can be realized using, for example, a DECI-ARC 3000 V gas tube from Reynolds Industries, Inc. Adjustable spark gaps provide the opportunity to adjust the output of the unipolar high voltage power supply and the intensity of the cold plasma device to which it is connected. In a further embodiment of the present invention that incorporates a sealed (and therefore non-adjustable) spark gap, thereby ensuring a stable plasma intensity.

In an exemplary embodiment of the unipolar high voltage power supply, a 555 timer 320 is used to provide a pulse repetition frequency of approximately 150-600 Hz. As discussed above, the unipolar high voltage power supply produces a series of spark gap discharge pulses based on the pulse repetition frequency. The spark gap discharge pulses have a very narrow pulse width due to the extremely rapid discharge of capacitive stored energy across the spark gap. Initial assessments of the pulse width of the spark gap discharge pulses indicate that the pulse width is approximately 1 nsec. The spark gap discharge pulse train can be described or modeled as a filtered pulse train. In particular, a simple resistor-inductor-capacitor (RLC) filter can be used to model the capacitor, high voltage coil and series resistance of the unipolar high voltage power supply. In one embodiment of the invention, the spark gap discharge pulse train can be modeled as a simple modeled RLC frequency response centered in the range of around 100 MHz. Based on the pulse repetition frequency of 192 Hz, straightforward signal analysis indicates that there would be approximately 2,000,000 individual harmonic components between DC and 400 MHz.

In another embodiment of the unipolar high voltage power supply described above, a 556 timer or any timer circuit can be used in place of the 555 timer 320. In comparison with the 555 timer, the 556 timer provides a wider frequency tuning range that results in greater stability and improved cadence of the unipolar high voltage power supply when used in conjunction with the cold plasma device.

Cold Plasma Iron Treatment Device

Figure 4:
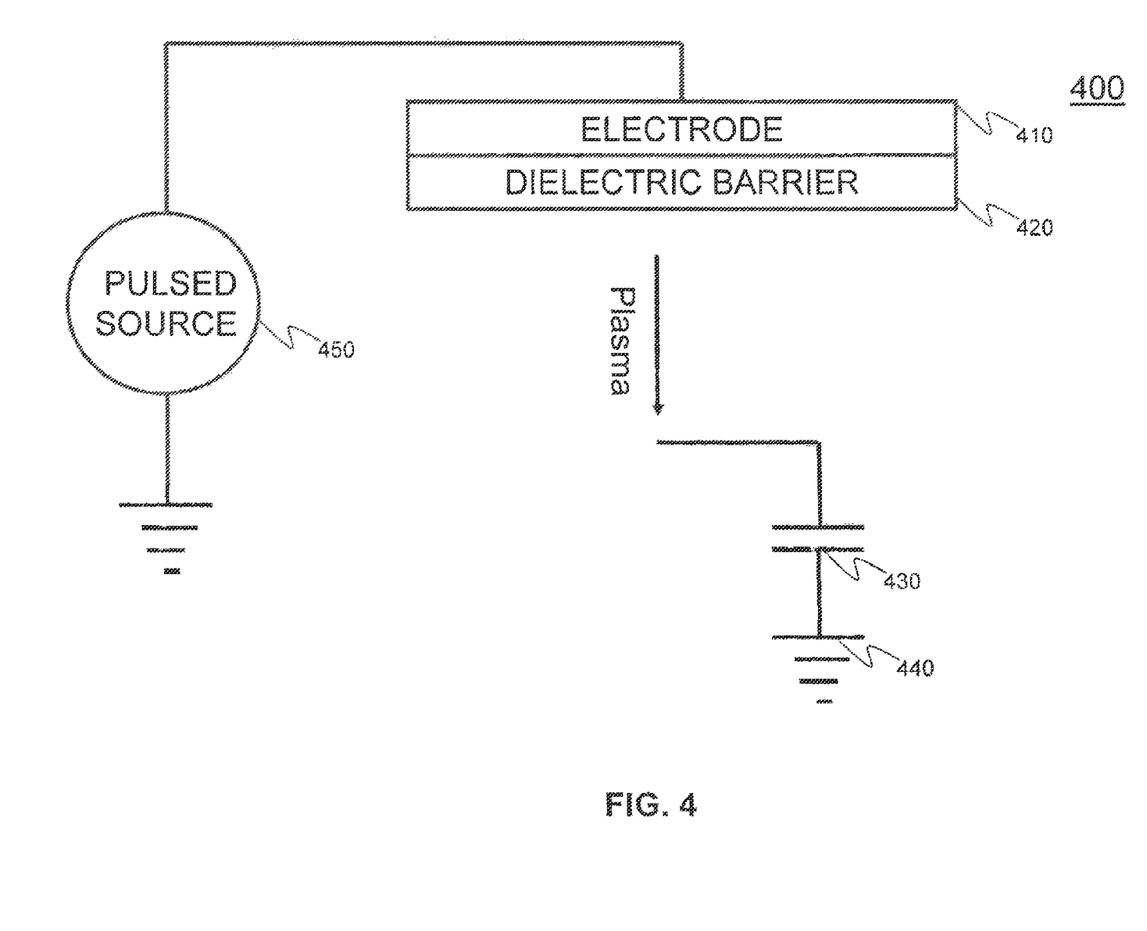
FIG. 4 illustrates the generation of cold plasma resulting using a dielectric barrier discharge principle, in accordance with embodiments of the present invention.

Devices, other than the cold plasma device illustrated above in FIG. 1, can also generate cold plasma. For example, cold plasma can also be generated by a dielectric barrier discharge device, which relies on a different process to generate the cold plasma. As FIG. 4 illustrates, a dielectric barrier discharge (DBD) device 400 contains one metal electrode 410 covered by a dielectric layer 420. The electrical return path 430 is formed by the ground 440 that can be provided by the target substrate undergoing the cold plasma treatment. Energy for the dielectric barrier discharge device 400 can be provided by a power supply 450, such as that described above and illustrated in FIG. 2. More generally, energy is input to the dielectric barrier discharge device in the form of pulsed electrical voltage to form the plasma discharge. By virtue of the dielectric layer, the discharge is separated from the metal electrode and electrode etching and gas heating is reduced. The pulsed electrical voltage can be varied in amplitude and frequency to achieve varying regimes of operation.

Figure 5:
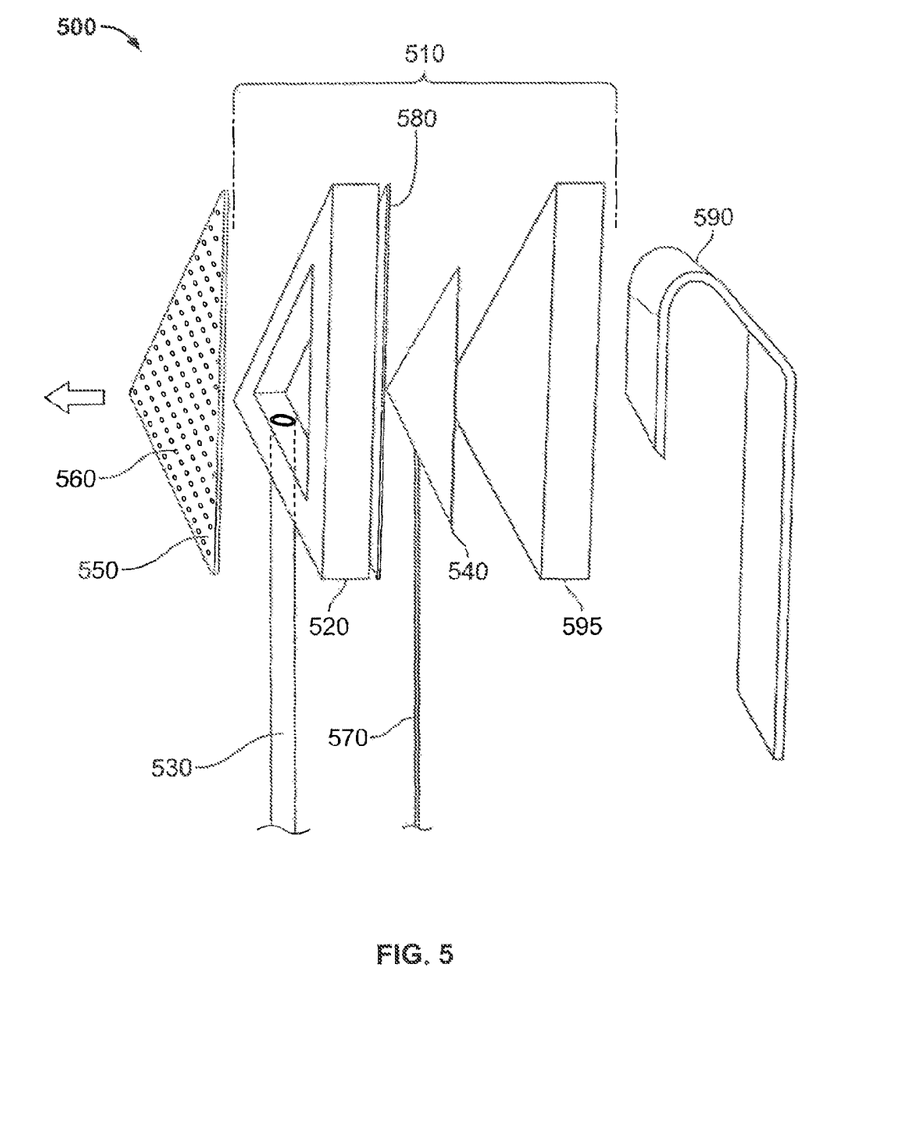
FIG. 5 illustrates a cold plasma treatment device, in accordance with an embodiment of the present invention.

In an exemplary embodiment of a cold plasma treatment device using the DBD principle, a "steam-iron" shaped cold plasma treatment device 500 is provided as shown in FIG. 5. Cold plasma treatment device 500 contains a body 510, a bottom member 550 and an optional handle 590. Body 510 contains gas compartment 520, which is connected to a gas inlet port 530. Adjacent to gas compartment 520 is a dielectric barrier 580, followed by an electrode 540, which is connected to a high voltage electrical port 570. Bottom member 550 contains a plurality of holes 560 through which cold plasma can exit from the gas compartment 520. In operation, a pulsed electrical voltage is applied to high voltage electrical port 570, while a suitable gas is applied to gas inlet port 530. The gas compartment 520 receives the applied gas, and the applied gas is energized by the electrode 540 in accordance with the DBD effect described above. The gas, which has a desired composition, has a short dwell time in the high energy field provided by electrode 540. The energized gas results in a cold plasma which exits the gas compartment 520 via the plurality of holes 560. Plurality of holes 560 can be formed by any means, including the use of open-cell foam.

Dielectric barrier 580 can be made of any suitable dielectric material to maintain the required insulation at the voltages used in the DBD effect. In an exemplary embodiment, dielectric barrier 580 can use a suitable dielectric material, such as ceramic, polytetrafluoroethylene (PTFE), quartz and the like. Similarly, the gas compartment 520 and other portions of the body 510 can also be manufactured using a suitable inert material, such as ceramic, PTFE, polyoxymethylene, polyamide-imides and the like. The gas used in cold plasma treatment device 500 can be any noble gas, or mixture of noble gases. In an exemplary device, the gas can be helium. Electrode 540 can be manufactured using any suitable conducting material. In an exemplary embodiment, electrode 540 can be any suitable conductive material. Suitable conductive materials include metals (e.g., brass), as well as plated conductive materials (e.g., nickel-plated, silver-plated, gold-plated, and the like, as well as combinations thereof). Bottom member 550 can be manufactured using any non-conductive material from which a plurality of holes can be formed, including open-cell foam. Element 595 can be any suitable dielectric material of suitable thickness to provide isolation of electrode 540 to preclude discharge of plasma via an unwanted path, e.g., via optional handle 590. Optional handle 590 can also be made using acrylic or any suitable non-conductive material.

Figure 6:
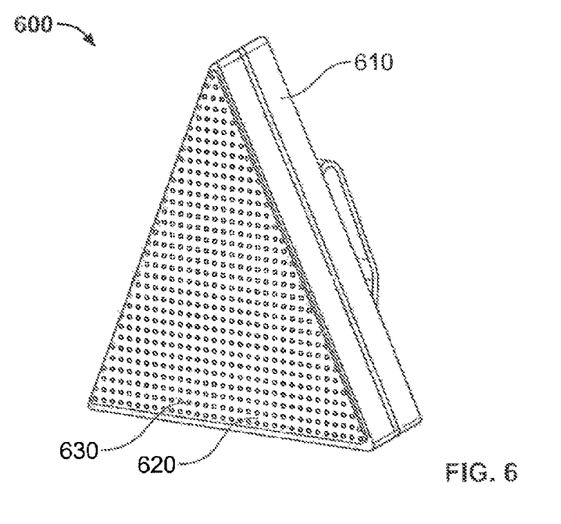
FIG. 6 illustrates the underside of a cold plasma treatment device, in accordance with an embodiment of the present invention.

Bottom member 550 is shown with a triangle shape that matches the shape of gas compartment 520. The triangle shape is exemplary, and other shapes fall within the scope of embodiments of the present invention. In other exemplary embodiments, polygonal and oval shapes are used. FIG. 6 illustrates a bottom view of cold plasma treatment device 600. Cold plasma treatment device 600 has body 610, bottom member 620, with the plurality of holes 630. Referring back to FIG. 5, gas compartment 520 and bottom member 550 can be any shape. In particular, the shape of gas compartment 520 and bottom member 550 can be chosen to be aligned to the shape of the desired treatment area. Thus, a triangle is one of many shapes that fall within the scope of this disclosure.

Bottom member 550 is shown to be a flat member. However, bottom member 550 can also be non-flat, i.e., a curvature that conforms to a non-flat treatment area. In a further embodiment, bottom member 550 can also have sufficient flexibility to be able to conform to a non-flat treatment area, such as a conformable open-celled foam.

Figure 7:
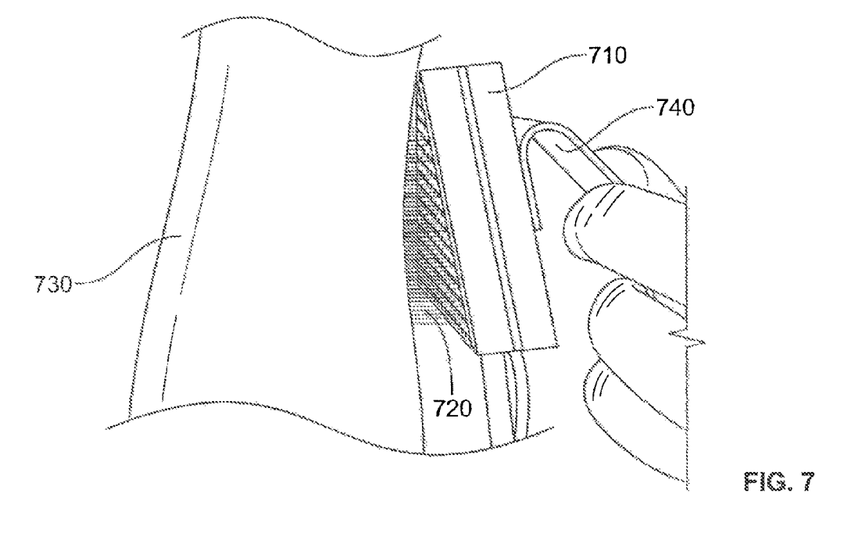
FIG. 7 illustrates the cold plasma emanating from the cold plasma treatment device, in accordance with an embodiment of the present invention.

FIG. 7 illustrates cold plasma treatment device 710 in operation. Cold plasma treatment device 710 that generates cold plasma streams 720 onto treatment surface 730. Optional handle 740 is also shown. As can be readily understood by one of skill in the art, other alternative means of handling cold plasma treatment device 710 are within the scope of the disclosure. Other alternative means include both manual manipulation as well as semiautomatic and automatic means of manipulation (e.g., semiautomatic and automatic actuators). Manipulation is used to apply the cold plasma treatment device 710 to the required treatment area.

The cold plasma treatment device 710 can be referred to as a "plasma iron." The term plasma iron comes from the overall shape of the plasma applicator. As seen above, it is of generally triangular shape with a plurality of holes on its lower face (directed toward the treatment area) through which multiple individual plasma plumes are directed. In the "plasma iron," there is a handle made of dielectric material, such as plastic or acrylic, on the face opposing the lower face, or bottom member of the "plasma iron." The "plasma iron" operates to generate atmospheric pressure cold plasma in a non-equilibrium mode. As noted above, the "plasma iron" uses a single plate type electrode separated from a flowing gas by a thin dielectric barrier of acrylic or similar material. The gas inlet directs the gas flow into a small void between the dielectric material and the plurality of holes on the lower face or bottom member. When the lower face is brought into proximity with a conductive body such as the treatment area, the energy is directed from the plate electrode, through the dielectric, into the gas, through the plurality of holes, and to the target body. In the process, the gas becomes ionized and flows through the plurality of ports as a plurality of cool plasma streams.

The arrangements described above combine some aspects of dielectric barrier discharge (DBD) plasmas with atmospheric pressure plasma jets (APPJ), such as that illustrated in FIG. 1, to create a unique effect. DBD plasmas are generally created in a non-equilibrium mode by passing electrical discharges over a small distance through ambient air. The electrode shape for a DBD plasma is generally demonstrated as a flat disk shape, or any shape of essentially two dimensions. APPJ may be generated as equilibrium or non-equilibrium plasmas but involve direct contact between the plasma energy source (electrode array) and the feed gas, generally in three dimensions (e.g., pin-in-tube electrode, cylindrical electrode). In this embodiment, a flat, plate-like, two-dimensional electrode is separated from a feed gas by a dielectric barrier, thus separating the electrode from the gas jet causing an ionized gas stream to exit the device in a controlled manner. This provides for a broad surface of plasma generation with the benefit of feed gas control allowing for subsequent optimization of the plasma chemistry and biological effects. The harmonic cold plasma power source design allows for this high level of ionization without substantial temperature rise. The combined effect of multiple simultaneous RF waveforms increases the ionization level of the gas while maintaining low overall gas temperatures. This device is powered by the same power supply unit as the '369 patent family.

Cold Plasma Iron Manufacturing and Usage Method

Figure 8:
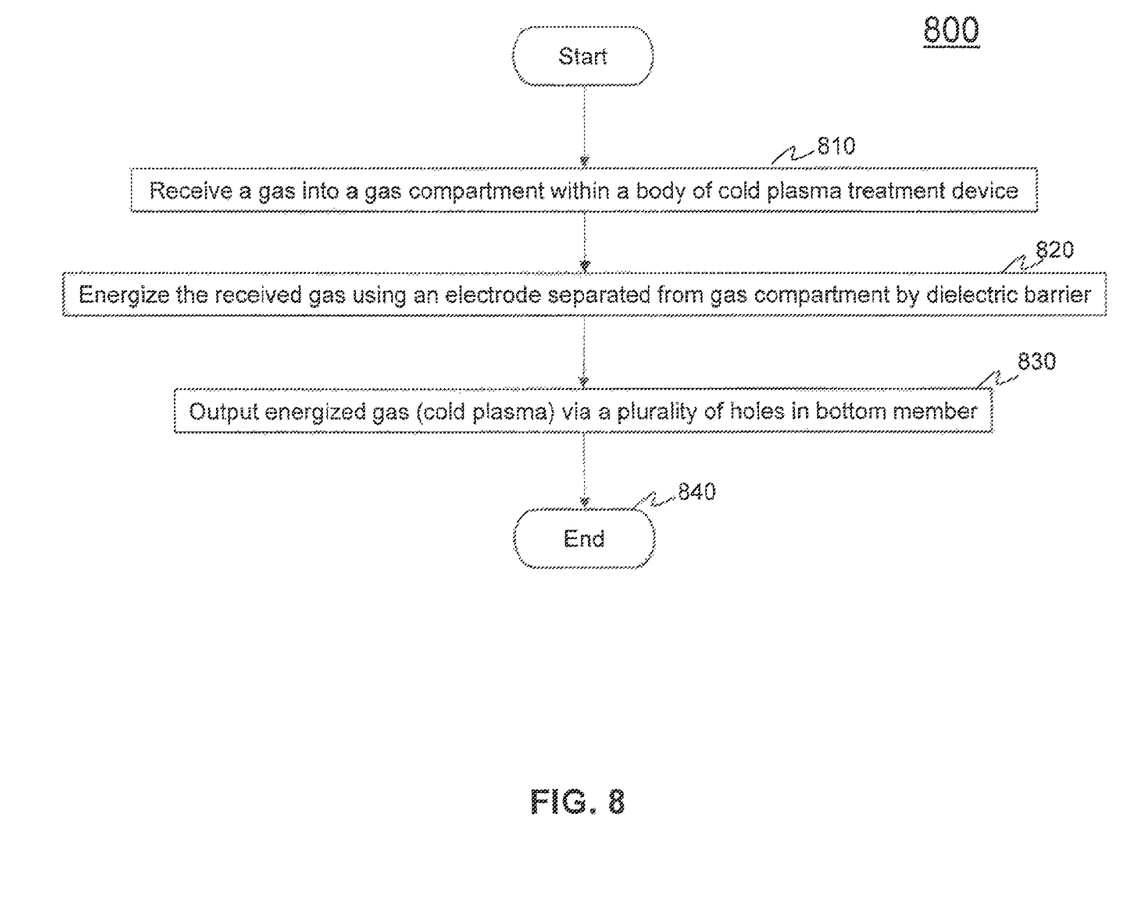
FIG. 8 illustrates a method of forming a cold plasma using a cold plasma treatment device, in accordance with an embodiment of the present invention.

FIG. 8 provides a flowchart of an exemplary method 800 to generate a cold plasma using a cold plasma treatment device, according to an embodiment of the present invention.

The process begins at step 810. In step 810, a gas is received into a gas compartment within a body of a cold plasma treatment device. In an embodiment, a gas is received into a gas compartment 520 within a body 510 of a cold plasma treatment device.

In step 820, the received gas is energized in the gas compartment to form a cold plasma, the electrical energy being applied via an electrical input port to an electrode adjacent to a dielectric barrier, the dielectric barrier sandwiched between the electrode and the gas compartment. In an embodiment, the received gas is energized in gas compartment 520 using energy from electrode 540 that is in turn received from electrical input port 570. Dielectric barrier 580 is sandwiched between electrode 540 and gas compartment 520.

In step 830, the gas is output via a plurality of holes in a bottom member. In an embodiment, the gas is output via a plurality of holes 560 in a bottom member 550.

At step 840, method 800 ends.

It is to be appreciated that the Detailed Description section, and not the Summary and Abstract sections, is intended to be used to interpret the claims. The Summary and Abstract sections may set forth one or more but not all exemplary embodiments of the present invention as contemplated by the inventor(s), and thus, are not intended to limit the present invention and the appended claims in any way.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

What is claimed is:

1. A cold plasma treatment device comprising:
   a body having a gas compartment therein, the gas compartment communicatively coupled to a gas inlet port;
   a bottom member comprises of a non-conductive material having a plurality of openings, the plurality of openings communicatively coupled to the gas compartment; and
   a dielectric barrier discharge device formed by an electrode disposed adjacent to an insulating barrier, the insulating barrier in turn disposed adjacent to the gas compartment and the electrode coupled to a high voltage electrical inlet port.

2. The cold plasma treatment device of claim 1, further comprising:
   a manipulation element attached to the body, wherein the manipulation element is one of a handle, a semi-automatic manipulation actuator, and an automatic manipulation actuator.

3. The cold plasma treatment device of claim 1, wherein the body comprises at least one of ceramic, PTFE, polyoxymethylene and polyamide-imides.

4. The cold plasma treatment device of claim 1, wherein the bottom member is flat.

5. The cold plasma treatment device of claim 1, wherein the bottom member is flexible.

6. The cold plasma treatment device of claim 1, wherein the electrode comprises metallic material.

7. The cold plasma treatment device of claim 1, wherein the bottom member is polygonal in shape.

8. The cold plasma treatment device of claim 1, wherein the bottom member comprises open-cell foam to form the plurality of openings.

9. A method comprising:
   receiving a gas into a gas compartment within a body, the gas received via a gas inlet port;
   energizing the received gas within the gas compartment to generate a cold plasma by applying electrical energy via an electrical input port to an electrode adjacent to a dielectric barrier, the dielectric barrier sandwiched between the electrode and the gas compartment; and
   outputting the cold plasma via a plurality of holes in a bottom member comprises of a non-conductive material, the plurality of holes communicatively coupled to the gas compartment.

10. The method of claim 9, further comprising:
    applying the cold plasma to a treatment area using a manipulation element, wherein the manipulation element is one of a handle, a semi-automatic manipulation actuator, and an automatic manipulation actuator.

11. The method of claim 9, wherein the body comprises at least one of ceramic, PTFE, polyoxymethylene and polyamide-imides.

12. The method of claim 9, wherein the bottom member is flat.

13. The method of claim 9, wherein the bottom member is flexible.

14. The method of claim 9, wherein the electrode comprises metallic material.

15. The method of claim 9, wherein the bottom member is polygonal in shape.

16. The method of claim 9, wherein the bottom member comprises a non-conductive material.

17. The method of claim 9, wherein the outputting the cold plasma via a plurality of holes in a bottom member includes using open-cell foam in the bottom member.

18. A cold plasma treatment system comprising:
   a body having a gas compartment therein, the gas compartment communicatively coupled to a gas inlet port;
   a bottom member comprises of non-conductive material having a plurality of openings, the plurality of openings communicatively coupled to the gas compartment;
   a barrier discharge device formed by an electrode disposed adjacent to an insulating barrier, the insulating barrier in turn disposed adjacent to the gas compartment and the electrode coupled to a high voltage electrical inlet port; and
   a pulsed electrical source coupled to the high voltage electrical inlet port.

19. The cold plasma treatment system of claim 18, further comprising:
   a source of gas coupled to the gas inlet port.

20. The cold plasma treatment device of claim 1, wherein a first surface of the bottom member and a second surface of the insulating barrier share a common shape.

21. The cold plasma treatment device of claim 1 wherein a first surface of the bottom member, a second surface of the insulating barrier and a third surface of the electrode have a same surface area.

22. The cold plasma treatment device of claim 1, wherein the electrode and the gas compartment are on opposing sides of the insulating barrier.

* * * * *

UNITED STATES PATENT AND TRADEMARK OFFICE
CERTIFICATE OF CORRECTION

| | |
|---|---|
| PATENT NO. | : 8,928,230 B2 |
| APPLICATION NO. | : 13/620224 |
| DATED | : January 6, 2015 |
| INVENTOR(S) | : Watson et al. |

It is certified that error appears in the above-identified patent and that said Letters Patent is hereby corrected as shown below:

In the Claims,

In column 8, line 20, replace "comprises of" with --comprising--.
In column 8, line 57, replace "comprises of" with --comprising--.
In column 9, line 16, replace "comprises of" with --comprising--.
In column 10, line 13, replace "claim 1" with --claim 1,--.

Signed and Sealed this
Twelfth Day of May, 2015

Michelle K. Lee
*Director of the United States Patent and Trademark Office*